United States Patent
O'Brien

(10) Patent No.: US 7,000,000 B1
(45) Date of Patent: Feb. 14, 2006

(54) POLYSACCHARIDE FIBERS

(75) Inventor: John P. O'Brien, Oxford, PA (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/857,572

(22) PCT Filed: Jan. 19, 2000

(86) PCT No.: PCT/US00/01160

§ 371 (c)(1),
(2), (4) Date: Jun. 5, 2001

(87) PCT Pub. No.: WO00/43580

PCT Pub. Date: Jul. 27, 2000

Related U.S. Application Data

(60) Provisional application No. 60/117,209, filed on Jan. 25, 1999.

(51) Int. Cl.
  *C07H 1/00*     (2006.01)
  *C07H 3/00*     (2006.01)
  *C08B 37/00*    (2006.01)

(52) U.S. Cl. .................... 536/123.12; 536/124
(58) Field of Classification Search ........... 536/123.12, 536/124
See application file for complete search history.

(56) References Cited

U.S. PATENT DOCUMENTS

| | | | |
|---|---|---|---|
| 4,072,567 A | | 2/1978 | Yokobayashi et al. |
| 4,109,663 A | * | 8/1978 | Maeda et al. ............... 131/359 |
| 4,306,059 A | | 12/1981 | Yokobayashi et al. |
| 4,501,886 A | | 2/1985 | O'Brien |
| 4,830,752 A | * | 5/1989 | Shibata et al. ............... 210/635 |

FOREIGN PATENT DOCUMENTS

| WO | WO 9606173 | 2/1996 |
|---|---|---|
| WO | WO 9940217 | 8/1999 |

OTHER PUBLICATIONS

Simpson et al., Microbiology, vol. 141, pp. 1451-1460 (1995).
Ogawa et al., Fiber Diffraction Methods, 47, pp. 353-362 (1980).
Applied Fibre Science, F. Happey, Ed., Chapter 8, E. Atkins, Academic Press, New York 1979.

* cited by examiner

*Primary Examiner*—James O. Wilson
*Assistant Examiner*—Everett White

(57) ABSTRACT

This invention pertains to novel fibers made of $\alpha(1\rightarrow3)$ polysaccharides, and a process for their production. The fibers of the invention have "cotton-like" properties but can be produced as continuous filaments on a year-round basis. The fibers are useful in textile applications.

15 Claims, 1 Drawing Sheet

US 7,000,000 B1

POLYSACCHARIDE FIBERS

CROSS-REFERENCE TO RELATED APPLICATIONS

This application is a U.S.C. 371 national phase entry of PCT International Application No. PCT/US00/01160, filed 19 Jan. 2000 which claims priority benefit from U.S. Provisional Application No. 60/117,209, filed 25 Jan. 1999.

BACKGROUND OF THE INVENTION

This invention pertains to novel fibers made of $\alpha(1\rightarrow 3)$ polysaccharides, and a process for their production. The fibers of the invention have "cotton-like" properties but can be produced as continuous filaments on a year-round basis. The fibers are useful in textile applications.

Polysaccharides have been known since the dawn of civilization, primarily in the form of cellulose, a polymer formed from glucose by natural processes via $\beta(1\rightarrow 4)$ glucoside linkages; see, for example, *Applied Fibre Science*, F. Happey, Ed., Chapter 8, E. Atkins, Academic Press, New York, 1979. Numerous other polysaccharide polymers are also disclosed therein.

Only cellulose among the many known polysaccharides has achieved commercial prominence as a fiber as a consequence of the many useful products derived therefrom. In particular, cotton, a highly pure form of naturally occurring cellulose, is well-known for its beneficial attributes in textile applications.

It is further known that cellulose exhibits sufficient chain extension and backbone rigidity in solution to form liquid crystalline solutions; see, for example O'Brien, U.S. Pat. No. 4,501,886. The teachings of the art suggest that sufficient polysaccharide chain extension could be achieved only in $\beta(1\rightarrow 4)$ linked polysaccharides and that any significant deviation from that backbone geometry would lower the molecular aspect ratio below that required for the formation of an ordered phase.

More recently, glucan polymer characterized by $\alpha(1\rightarrow 3)$ glucoside linkages has been isolated by contacting an aqueous solution of sucrose with GtfJ glucosyltransferase isolated from *Streptococcus salivarius*, Simpson et al., Microbiology, vol 141, pp. 1451–1460 (1995). Highly crystalline, highly oriented, low molecular weight films of $\alpha(1\rightarrow 3)$-D-glucan have been fabricated for the purposes of x-ray diffraction analysis, Ogawa et al., Fiber Diffraction Methods, 47, pp. 353–362 (1980). In Ogawa, the insoluble glucan polymer is acetylated, the acetylated glucan dissolved to form a 5% solution in chloroform and the solution cast into a film. The film is then subjected to stretching in glycerine at 150° C. which orients the film and stretches it to a length 6.5 times the original length of the solution cast film. After stretching, the film is deacetylated and crystallized by annealing in superheated water at 140° C. in a pressure vessel. It is well-known in the art that exposure of polysaccharides to such a hot aqueous environment results in chain cleavage and loss of molecular weight, with concomitant degradation of mechanical properties. Thus, considerable benefit would accrue to a process which would provide the high orientation and crystallinity desired for fibers without a reduction in molecular weight.

It is highly desirable to discover other polysaccharides having utility as films, fibers or resins because of their widespread importance in the global ecosystem. Polysaccharides based on glucose and glucose itself are particularly important because of their prominent role in photosynthesis and metabolic processes. Cellulose and starch, both based on molecular chains of polyanhydroglucose are the most abundant polymers on earth and are of great commercial importance. Such polymers offer materials that are environmentally benign throughout their entire life cycle and are constructed from renewable energy and raw materials sources.

The properties exhibited by cellulose and starch are determined by the nature of their enchainment pattern. Hence, starch or amylose consisting of $\alpha(1\rightarrow 4)$ linked glucose is not useful for fiber applications because it is swollen or dissolved by water. Alternatively, cellulose, having $\beta(1\rightarrow 4)$ enchainment, is a good structural material being both crystalline and hydrophobic, and is commonly used for textile applications as cotton fiber. Like other natural fibers, cotton has evolved under constraints, wherein the polysaccharide structure and physical properties have not been optimized for textile uses. In particular, cotton fiber offers short fiber length, limited variation in cross section and fiber fineness and is produced in a highly labor and land intensive process.

Thus, it is desirable to form new structural polysaccharides through processes such as enzymatic synthesis or through genetic modification of microorganisms or plant hosts and fibers made from such new polysaccharides that retain the desirable features of biodegradability, renewable resource-based feedstocks and low cost.

SUMMARY OF THE INVENTION

The present invention concerns a polysaccharide fiber, comprising: a polymer comprising hexose units wherein at least 50% of the hexose units are linked via an $\alpha(1\rightarrow 3)$ glycoside linkage, said polymer having a number average degree of polymerization of at least 100.

The present invention also concerns a process for producing a polysaccharide fiber, comprising the steps of: dissolving a sufficient amount of a polymer comprising hexose units, wherein at least 50% of the hexose units are linked via an $\alpha(1\rightarrow 3)$ glycoside linkage, in a solvent or in a mixture comprising a solvent to form a liquid crystalline solution, and spinning a polysaccharide fiber from said liquid crystalline solution.

The present invention further concerns a liquid crystalline solution, comprising: a solvent and an amount sufficient to form liquid crystals of a polymer comprising hexose units wherein within the polymer at least 50% of the hexose units are linked via an $\alpha(1\rightarrow 3)$ glycoside linkage.

DETAILED DESCRIPTION

Figure 1:
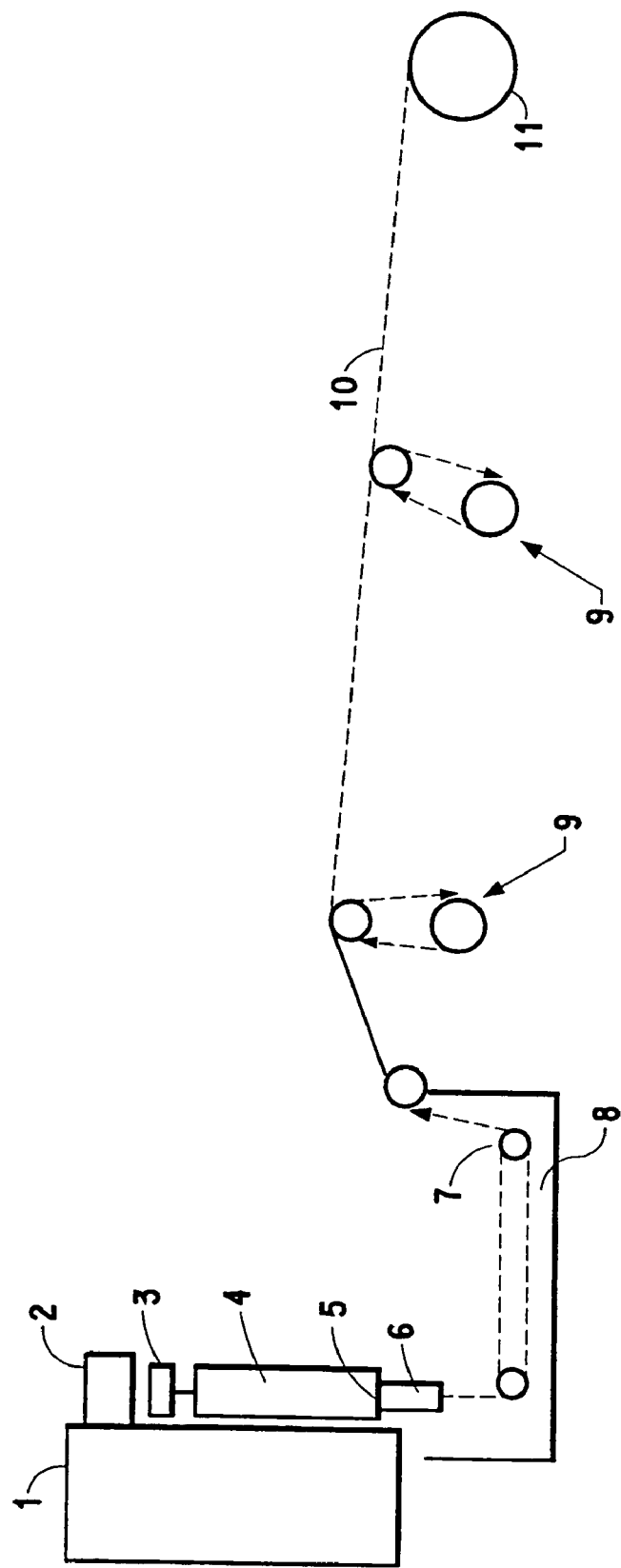
FIG. 1 is a schematic diagram of an apparatus for air gap or wet spinning of liquid crystalline solutions of hexose polymer to form polysaccharide fibers.

In one of the surprising aspects of the present invention, it has now been found that a polymer comprising hexose units, wherein at least 50% of the hexose units within the polymer are linked via an $\alpha(1\rightarrow 3)$ glycoside linkage, can form a liquid crystalline solution when a sufficient amount of the polymer is dissolved in a solvent or in a mixture comprising a solvent, and that from this solution can be spun a continuous, high strength, cotton-like fiber highly suitable for use in textiles either in a derivatized form, a non-derivatized form or a regenerated form. By "regenerated" is meant that any derivative groups added during the preparation of the fiber are removed.

Suitable for use in the present invention are hexose polymers comprising repeating hexose monomer units wherein at least 50% of the hexose units are linked by an α(1→3) glycoside linkage. Such hexose polymers include those formed from the monomers glucose, fructose, mannose, galactose, combinations thereof, and mixtures of any of the foregoing. A linkage involving a glucose monomeric unit can be called a glucoside linkage. Polyhexose polymers used herein include both the dextrorotatory (D) and levorotatory (L) enantiomers of such polymers as well as racemic mixtures thereof. Preferred are the D-forms; most preferred is D-glucose. A racemic mixture is less preferred.

By "α(1→3) glycoside linkage" is meant that within the polymer, the repeating monomeric units are linked in a particular manner dictated by an enchainment pattern. The nature of the enchainment pattern depends, in part, on how the ring closes when an aldohexose ring closes to form a hemiacetal. The open chain form of glucose (an aldohexose) has four asymmetric centers (see below). Hence there are $2^4$ or 16 possible open chain forms of which D and L glucose are two. When the ring closes, there is a new asymmetric center created at C1 thus making 5 asymmetric carbons. Depending on how the ring closes, for glucose, α(1→4)-linked polymer, e.g. starch or β(1→4)-linked polymer, e.g. cellulose can be formed upon further condensation to polymer. The configuration at C1 in the polymer determines whether it is an alpha or beta linked polymer, and the numbers in parenthesis following alpha or beta refer to the carbon atoms through which enchainment takes place.

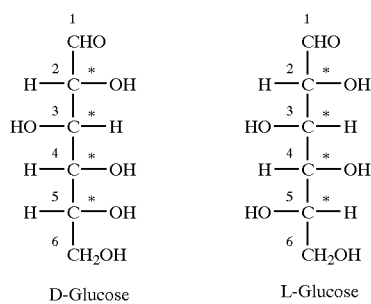

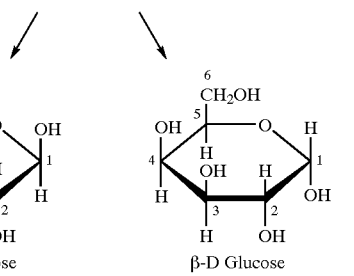

α-D Glucose   β-D Glucose

* asymmetric carbon center

The polymer used to form the polysaccharide fiber of the present invention possesses a number average degree of polymerization of at least 100 and can range up to about 5,000. Preferably, the number average degree of polymerization ranges from about 200 to about 1,000.

The polysaccharides of the present invention can be homoglycans or heteroglycans. If only one type of hexose unit is used during preparation of the polysaccharide, a homoglycan is formed. Glucan is a homoglycan formed from glucose. If more than one type of hexose unit is used, a heteroglycan is formed.

The polymer of the polysaccharide fibers of the present invention can further comprise monomer units other than hexose units, such as pentoses. It is preferred that substantially all of the monomer units within the polymer in the present invention are hexose monomer units. By "substantially all" is meant at least 90%.

In a similar vein, the polysaccharide fibers of the present invention can further comprise monomer units linked by a glycoside linkage other than α(1→3), such as α(1→4), α(1→6), β(1→2), β(1→3), β(1→4) or β(1→6) or any combination thereof. At least 50% of the glycoside linkages in the polymer are an α(1→3) glycoside linkage. Preferably, substantially all of the linkages are α(1→3) glycoside linkages, and most preferably all of the hexose units in the polymer are linked by an α(1→3) glycoside linkage. By "substantially all" is meant at least 90%.

The polysaccharide fibers of the present invention are produced by dissolving the polymer, described above, in a solvent or in a mixture comprising a solvent, to form a liquid crystalline solution. Oriented fiber is then spun from the liquid crystalline solution.

The isolation and purification of various polysaccharides is described in, for example, *The Polysaccharides*, G. O. Aspinall, Vol. 1, Chap. 2, Academic Press, New York, 1983. In a preferred embodiment of the present invention, poly(α (1→3)-D-glucose) is formed by contacting an aqueous solution of sucrose with GtfJ glucosyltransferase isolated from *Streptococcus salivarius* according to the methods taught in the art. Any method which results in a purity of ca. 90% or greater is satisfactory. One such method is provided in detail hereinbelow.

The polymer comprising hexose units can be derivatized, preferably acetylated, most preferably close to 100% acetylated, in order to facilitate rendering the polysaccharide soluble in the spinning solvent to achieve a solids level sufficient for liquid crystals to form. For examples of representative polysaccharide derivatives useful herein, see *The Polysaccharides*, G. O. Aspinall, Vol. 2, Chap. 2, Academic Press, New York, 1983. Preferred derivatives include methyl, ethyl, hydroxyethyl, nitrate, acetate, proprionate and butyrate. A preferred derivatized polymer is a poly(α(1→3)-D-glucose acetate). Acetylation can be accomplished using the method described by O'Brien, op.cit., for acetylating cellulose. It can be useful to pre-activate the hexose polymer by first contacting it with acetic acid prior to its contact with an acetylation mixture such as a mixture of glacial acetic acid, acetic anhydride, and methylene chloride. Contact with the mixture is followed by the addition of perchloric acid to initiate esterification.

Following optional formation of the derivative, the polymer is dissolved in a solvent or in a mixture comprising a solvent to form a liquid crystalline solution. By "liquid crystalline solution" is meant a solution in which a spontaneous phase separation from randomly dispersed polymer molecules to domains of locally ordered molecules has occurred. Formation of the liquid crystalline solution is dependent on the solids content of the polymer so dissolved. "Solids content" refers to the amount of dry polymer before it is dissolved. It is calculated as the (wt. of polymer)/(wt. of polymer+wt. of solvent). A liquid crystalline solution must be formed in order to obtain an oriented fiber when the solution is spun. The amount of polymer needed to provide a solids content sufficient for liquid crystals to form depends on the polymer morphology and the polymer molecular weight. The onset of liquid crystallinity can be determined by an observable increase in the birefringence of the solution being formed. Birefringence can be determined by any convenient means as are known in the art.

Non-derivatized polymers and the derivatized polymers formed as described above are soluble in solvents including organic halides, organic acids, fluorinated alcohols, or mixtures thereof. Representative of such solvents are methylene chloride (dichloromethane), trifluoroacetic acid, trichloroacetic acid, dichloroacetic acid, formic acid, hexafluoroisopropanol, and mixtures such as trifluoroacetic acid/methylene chloride, trichloroacetic acid/methylene chloride, dichloroacetic acid/methylene chloride, and formic acid/methylene chloride. Other suitable solvents include molecules which are nonsolvents by themselves (e.g., water) in combination with strong organic acids, such as trifluoroacetic acid/water, trichloroacetic acid/water, dichloroacetic acid/water, or formic acid/water. Preferably, an acetylated polymer is dissolved in a mixture of trifluoroacetic acid and methylene chloride, most preferably as a 60/40 v/v. mixture of trifluoroacetic acid and methylene chloride, respectively, at a temperature between about 0 and about 25° C. while mixing, preferably mixing under high shear.

The particular benefits of the present invention are achieved by virtue of the formation of the liquid crystalline solution comprising a solvent and an amount sufficient to form liquid crystals of a polymer comprising hexose units wherein at least 50% of the hexose units are linked via an α(1→3)glycoside linkage from which a highly oriented, highly crystalline continuous filament can be drawn. A preferred liquid crystalline solution is one wherein substantially all of the hexose units are linked via an α(1→3) glycoside linkage. A preferred polymer for a liquid crystalline solution is poly(α(1→3)-D-glucose acetate). One of skill in the art will understand that the minimum polymer concentration (solids content) required for achieving the formation of the liquid crystalline phase will vary according to the specific molecular morphology and the molecular weight of the polymer. A liquid crystalline solution having a solids content of at least 10% is preferred. A solids content ranging from about 10% to about 35% is more preferred herein, and most preferred is about 20 to about 35%. In a preferred embodiment of the present invention, it has been found that the minimum polymer concentration for phase separation of 100% poly(α(1→3)-D-glucose) is ca. 15% by weight in a 60/40 mixture of trifluoroacetic acid and methylene chloride when the number average molecular weight of the polymer is ca. 60,000 Daltons. Optimum spinning performance for this particular polymer is achieved at about 20 to about 30% by weight solids content, which is most preferred.

Spinning from the liquid crystalline solution can be accomplished by means known in the art, and as described in O'Brien, op.cit. The viscous spinning solution can be forced by means such as the push of a piston or the action of a pump through a single or multi-holed spinneret or other form of die. The spinneret can be of any cross-sectional shape, including round, flat, multi-lobal, and the like, as are known in the art. The extruded strand can then be passed by ordinary means into a coagulation bath wherein is contained a liquid which dissolves the solvent of the spinning solvent but not the polymer thereof, thus causing the highly oriented polymer to coagulate into a fiber according to the present invention.

Under some circumstances, a superior result is achieved when the extruded strand first passes through an inert, noncoagulating layer, usually an air gap, prior to introduction into the coagulation bath. When the inert layer is an air gap, the spinning process is known as air-gap spinning. Under other circumstances, extrusion directly into the coagulation bath is preferred, known as wet-spinning. Preferred solvents for the coagulation bath include aliphatic alcohols, particularly methanol, ethanol, or isopropanol.

FIG. 1 is a schematic diagram of an apparatus for wet or air-gap spinning of polysaccharide fibers. Syringe pump 1 drives ram 2 at a controlled rate onto piston 3 of spinning cell 4. A suitable syringe pump is a Harvard model 44. Spinning cell 4 can contain a metal filter, such as a Dynalloy® X5, 10 μm sintered metal filter, above spinneret 6. Extrudate 12 is optionally directed through an inert noncoagulating layer and into liquid coagulating bath 8 and directed back and forth between guides 7 which, for example, can be ceramic or comprise Teflon® fluoropolymer. On exiting the coagulation bath, the extrudate can be optionally directed through a drawing zone between two independently driven rolls 9 and collected on bobbins, preferably stainless steel, at wind-up 11.

If in a derivatized form, the polysaccharide fibers of the present invention can be retained in such derivatized form. However, it is preferred to regenerate such fibers by converting them back to the hydroxyl reconstituted form. This can be accomplished by numerous means known in the art, such as by contacting the polysaccharide fiber with an excess of a saponification or hydrolysis medium. One deacetylation means found to be satisfactory herein is base-catalyzed saponification. For example, the acetylated fiber can be contacted with 0.05 molar methanolic sodium methoxide, or with a dilute aqueous base solution, such as 5% aqueous sodium or potassium hydroxide, for 24–72 hours at room temperature, to remove ester groups, such as the acetyl group.

It is quite surprising that poly(α(1→3)-D-glucose) forms liquid crystalline solutions, and that the highly desirable fibers of the present invention can be spun therefrom. Likewise for other polyhexoses comprising at least 50% α(1→3) glycoside linkages in combination with other non preferred linkages, liquid crystalline behavior can be observed. For example, Nigeran which includes α(1→3) and α(1→4) glycoside linkages can be dissolved in a solvent to form a liquid crystalline solution. However, other α-linked polyglucoses, especially those containing substantially all α(1→6) or α(1→4) linkages, and more generally other α-linked polysaccharides do not exhibit similar behavior, for example amylose (starch) which has α(1→4) linkages, dextran with α(1→6) linkages, and pullulan with α(1→4) and α(1→6) linkages.

The white, lustrous fibers of the present invention are characterized by a tensile strength of at least 1 gram per denier, preferably 2 grams per denier.

EXAMPLES

Polymer Isolation

In the examples following, except Example 7, two batches of poly(α(1→3)-D-glucose) were employed, designated P1 and P2.

P1 was produced according to the following sequence. The mature peptide encoded by the gtf-J gene of *Streptococcus salivarius* (strain ATCC 25975) was cloned by PCR amplification of template DNA from *Streptococcus salivarius* using primers based on the gene sequence described in Genbank accession number Z11873 and by Giggard et al., J. Gen. Microbiol. 137 (Pt 11), 2577–2593 (1991).

PCR reactions were run using the 5' primer SEQ ID NO:1:

5'-GGGAATTCCATATGAACATTGATGG-
TAAATATTAC where SEQ ID NO:2, the sequence:

AACATTGATGGTAAATATTAC corresponds to bases 555 through 547 of Genbank accession number Z11873 and the remaining 5' bases provide an Nde I recognition site and a few 5' bases to allow digestion of the PCR product with Nde I.

The 3' primer SEQ ID NO:3 had the sequence (read 5' to 3')

5'-AGATCTAGTCTTAGTTTAGCACTCTAGGTGG where SEQ ID NO:4 the sequence:

TTAGTTTAGCACTCTAGGTGG corresponds to the reverse compliment of bases 4559 through 4580 in Genbank accession number Z11873 and the remaining bases provide an Xba I site and extra bases to allow digestion of the PCR product with Xba I.

The PCR product was digested with Nde I and Xba I then purified by agarose gel electrophoresis and isolated. The fragment was ligated into the *E. coli* protein expression vector pET24a (Novagen) that had been digested with Nde I and Nhe I. The ligation reaction was used to transform *E. coli* cell line DH10B, and six clonal colonies from that transformation were grown and plasmid DNA was isolated. The plasmid DNA from each of these lines was used to transform *E. coli* cell line DE3.

Single colonies from each transformation were grown overnight in rich media, the resultant culture was diluted to about 0.05 optical density units at 600 nm and then re-grown to 2 optical density units at 600 nm then protein expression from the pET24a plasmid was induced by the addition of 1 mM isopropylthiogalactoside. Cells were harvested by centrifugation after 3 hr, re-suspended in 50 mM $KPO_4$ buffer at pH 6 which also contained 0.2 mM phenylmethylsulfonyl fluoride and disrupted by sonication.

Clonal cultures producing active dextran sucrase were identified by adding 10 ml of the cell extract to 50 mM sucrose and 0.5 mg ml-1 T-10 dextran (Sigma) in a total reaction volume of 100 ml of 50 mM $KPO_4$ buffer. Active clones producing enzyme polymerize glucose using sucrose as the glucosyl donor and producing insoluble polymer thus clouding the reaction solution within about 10 minutes. The polymer was lyophilized to form a dry powder.

P2 was produced in a larger scale modification of the process for producing P1. Production of the crude enzyme was done by scaling the procedure employed for the production of P1 to two one-liter cultures in shake flasks. Isolated cells were disrupted by French Press disruption using the buffer system described above. The cell extract was diluted to 10 mg of protein ml-1, brought to 30% saturation with ammonium sulfate and centrifuged to remove a small amount of precipitate. The supernatant was brought to 70% saturation in ammonium sulfate and the precipitated protein isolated by centrifugation. The protein pellet was stored as a suspension in 70% saturated ammonium sulfate and used as the suspension.

Poly ($\alpha(1\rightarrow 3)$-D-glucose) was produced by adding the ammonium sulfate suspension to a 2 l solution of 200 mM sucrose in 50 mM $KPO_4$ buffer pH 6 and stirring overnight at 28° C. The insoluble glucose polymer produced was removed from solution by centrifugation, re-suspended in water (500 ml) and again centrifuged. The water wash was repeated two more times and the centrifuge pellet was concentrated by vacuum filtration on a sintered glass filter. The filter cake was stored at 4° C. prior to use.

Testing Methods

Physical properties such as tenacity, elongation and initial modulus were measured using methods and instruments conforming to ASTM Standard D 2101-82, except that the test specimen length was one inch. Reported results are averages for 3 to 5 individual filament tests.

Example 1

2.86 g of wet polymer P2 was boiled in 150 ml deionized water for 1 h. After cooling, the product was collected by filtration and washed 3× with glacial acetic acid. The polymer, still wet with acetic acid, was suspended in a prechilled (–25° C.) acetylating mixture consisting of acetic anhydride (20 ml), glacial acetic acid (14 ml) and methylene chloride (20 ml). Mechanical stirring was started and 70% aqueous perchloric acid (0.2 ml) was added to initiate esterification. The reaction mixture was allowed to warm to 0° C. and held there for 3 h. The reaction mixture was subsequently allowed to warm to room temperature and held for 1 h, then frozen in dry ice overnight, and then warmed to room temperature again.

The viscous, homogeneous solution of thus acetylated P2 polymer was precipitated in methanol with rapid stirring and collected by filtration. The filtrate was thoroughly washed twice with methanol, then five times with deionized water, and then four times with methanol. The washed product was collected by filtration and allowed to air dry yielding 1.78 g of purified acetylated polymer which was soluble in methylene chloride. Size exclusion chromatography in hexafluoroisopropanol containing 0.1 M sodium triflate was conducted through two Showdex 80M columns yielding relative molecular weight values of $M_n$=60,800 and $M_w$=202,300.

1.5 g of the thus prepared $\alpha(1\rightarrow 3)$ glucan acetate was combined with 2.79 g of a solvent mixture consisting of 100 parts by weight trifluoroacetic acid (99%) and 8 parts by weight deionized water to form a 35% solids solution. In order to dissolve the polymer therein, the mixture of polymer and solvent was first stirred by hand using a stainless steel spatula in order to homogenize the mixture. The homogenized mixture was then pumped back and forth between two syringes connected by a short length of 3 mm ID stainless steel tubing. Dissolution of the polymer in the solvent mixture was complete within 4 h at room temperature. The solution was examined microscopically through crossed polarizers and found to be highly birefringent, confirming an oriented, lyotropic liquid crystalline phase.

The liquid crystalline solution so formed was transferred into a vertically positioned polyethylene syringe fitted with a Dynalloy® X5 sintered stainless steel filter available from Fluid Dynamics/Memtec Group, Deland, Fla. Trapped air was allowed to migrate to the top of syringe and vented during installation of the syringe plunger. This assembly was then fitted to a vertically mounted Harvard model 55-1144 syringe pump for controlled rate extrusion according to the parameters given in Table 1. The syringe was fitted with a stainless steel single hole spinneret having a hole diameter of 0.005 inches and capillary length of 0.010 inches. The face of the spinneret was maintained 0.5 inches above the surface of the methanol coagulation bath. The filament was extruded at 20 ft/min, drawn into the bath and directed around ceramic guides at both ends of the coagulation tray to obtain a total travel in the bath of 14 feet. (See FIG. 1) The coagulated fiber, still wet with methanol, was wound onto stainless steel bobbins at 58 ft/min. The bobbins were soaked in methanol overnight and the filaments were allowed to air dry before mechanical testing. As spun filament tenacity/elongation/modulus values were 4.2/17.5/53.9 grams per denier/percent/grams per denier, respectively.

Example 2

The as-spun fiber of Example 1 was deacetylated to yield regenerated poly ($\alpha(1\rightarrow3)$-D-glucose) fibers with good mechanical properties. A small skein of the fiber of Example 1 was immersed in a large excess of 0.05 M methanolic sodium methoxide and allowed to stand at room temperature for 24–72 h under nitrogen. The skein was removed, washed with methanol, blotted and air dried. Filament tenacity/elongation/modulus values were 2.7/12.5/51.3 grams per denier/percent/grams per denier, respectively.

Example 3

1.0 g of dried powder of P1 polymer was suspended in deionized water and boiled under nitrogen for 2 h. After cooling, the powder was collected by filtration and pressed to yield a wet filter cake. This was subsequently immersed in 100 ml of glacial acetic acid, stirred for 5 minutes at room temperature and collected by filtration. The acetic acid rinse was repeated and the powder was collected and pressed to remove excess acetic acid.

The filter cake was then added to a chilled (−25° C.) acetylation medium consisting of acetic anhydride (10 ml, 99.7%), glacial acetic acid (7 ml) and dichloromethane (10 ml). Perchloric acid (0.1 ml, 70%) was added and the reaction maintained with stirring at a temperature in the range of −30° C. to −2° C. for 6 h and then allowed to warm to 24° C. and held for 30 min. The resulting viscous mixture was precipitated into rapidly stirred methanol and then filtered. The filter cake was then washed once with methanol, followed by two washings with deionized water and then once with acetone. After drying, the yield was 1.2 g of purified acetylated polymer in the form of an off-white flake.

1 g of the thus prepared acetylated polymer was suspended in 3 g of a 60%/40% by volume mixture of trifluoroacetic acid (99%) and dichloromethane. After the polymer was dispersed in the solvent, the solution was mixed as described in Example 1. The resulting solution was lyotropic and highly fiber forming. The thus formed liquid crystalline solution was transferred to a polyethylene syringe fitted with a filter and extruded using the same general procedure as for Example 1. The filament was extruded at 10.4 fpm through a 0.5 inch air gap into methanol (bath length=13 ft) and wound up at 36 ft/min. As-spun filament tenacity/elongation/modulus values were 1.6/11.7/34.5 grams per denier/percent/grams per denier, respectively.

Example 4

A 6" skein of the as-spun filament of Example 3 was prepared from 5 wraps of continuous filament and the ends were tied together. A 50 g weight was suspended from the bottom of the skein (consisting of 10 total filaments) and the assembly was immersed in a large excess of 0.05 m methanolic sodium methoxide and maintained under nitrogen for 96 h. The filament was removed, washed by immersion in fresh methanol and allowed to air dry. The thus regenerated or deacetylated filament tenacity/elongation/modulus values were 2.4/13.0/52.2 grams per denier/percent/grams per denier, respectively.

Example 5

Poly ($\alpha(1\rightarrow3)$-D-glucose) acetate fibers were prepared as described in Example 3, except that the wind-up speed was 23 ft/min and the coagulation bath temperature was 3° C. As-spun filament tenacity/elongation/modulus values were 1.9/14.2/32.7 grams per denier/percent/grams per denier, respectively.

Example 6

Polymer P1 (2.0 g) was added as a dried powder to a chilled (0° C.) mixture of glacial acetal acid (99%, 14 ml), acetic anhydride (99.7%, 10 ml) and dichloromethane (20 ml). The reactants were kept under nitrogen and a catalyst solution at 0° C. of perchloric acid (70% aqueous, 0.2 ml) in acetic anhydride (10 ml) was added dropwise with rapid stirring. After addition of the catalyst solution, the reactants were allowed to warm to room temperature and stirred for 5 h. The amber-colored viscous solution thus formed was precipitated into methanol. The filter cake was washed twice with methanol, collected by filtration and vacuum dried at 50° C. to yield 2.65 (g) of off-white polymer flake.

1.0 g of the thus acetylated polymer was dissolved in trifluoroacetic acid/dichloromethane (60/40 v/v, 4.0 g) and mixed using the method of Example 1. The resulting solution was lyotropic and fiber forming. Extrusion was carried out using the general procedures described in Example 1, and the specific conditions in Table 1 below, except that it was wet-spun. As-spun filament tenacity/elongation/modulus values were 0.94/14.4/23.1 grams per denier/percent/grams per denier, respectively.

Example 7

Nigeran (an alternating $\alpha(1\rightarrow3)$, $\alpha(1\rightarrow4)$ glucan), 0.86 g (from *Asperigillus japonicus*, Cat #N2888, Sigma-Aldrich Co.) was suspended in 50 ml of glacial acetic acid for 20 min and collected by filtration. This step was repeated once more and the starting material (still wet with acetic acid) was added to a three necked flask containing the acetylation medium prechilled to 2° C. and fitted with a thermocouple, stirrer and nitrogen inlet tube. The acetylation medium consisted of acetic anhydride (20 ml), glacial acetic acid (14 ml) and methylene chloride (20 ml). Perchloric acid, (0.2 ml, 70% aqueous) was then added dropwise with rapid stirring while maintaining the temperature between 2–5° C. The reaction was maintained at this temperature for 3 h and subsequently allowed to warm to room temperature for an additional 3 h. The acetylated polymer was then isolated by precipitation into methanol, and collected by filtration. Additional washings with methanol (2 times) were conducted yielding 0.96 g of a white product.

A 30% solids solution of the above polymer in trifluoroacetic acid/water (100/8 w/w) was prepared and observed to be birefringent when viewed through crossed polarizing filters verifying the existence of a liquid crystalline solution.

Comparative Example 1

0.5 g of the purified acetylated polymer of Example 6 was dissolved in trifluoroacetic acid/dichloromethane (60/40 v/v, 2.8 g) using the method of Example 1. The resulting solution was not lyotropic (a liquid crystalline solution did not form) because the solids content was below the critical concentration for liquid crystalline phase separation, and was poorly fiber forming. Filament extrusion was carried out as described for Example 4 and the specific conditions in Table 1. As-spun fibers were soaked in methanol for 24 h before being dried and tested. As-spun filament tenacity/elongation/modulus values were 0.54/17.2/17.4 grams per denier/percent/grams per denier, respectively.

Comparative Example 2

A skein of the as-spun filament of Comparative Example 1 was deacetylated in 0.05 m methanolic sodium methoxide using the procedure described in Example 2. Filament tenacity/elongation/modulus values were 0.4/2.5/25.1 grams per denier/percent/grams per denier, respectively. Thus, regeneration of the poorly oriented isotropically spun precursor fiber gave a poor fiber.

Comparative Example 3

Preparation of Debranched Amylose

α(1→6) branch points were enzymatically removed from common corn starch as follows. 300 g of corn starch was gelatinized by heating in 8 L of water at 100° C. for 1 hour. The gelatinized starch was cooled to 50° C. and 50 ml of 1 M acetic acid was added to adjust the pH to about 4. 1 million units of isoamylase (Sigma) were added in 25 ml of sodium acetate buffer (50 mM, pH 4.5) and the mixture was incubated at 45° C. for 4 hours.

1.2 L of butanol was added to the above reaction mixture, and the mix was boiled for 1 hour. The mixture was then allowed to cool to room temperature slowly overnight. The mixture was further cooled to 5° C. and the precipitate was collected by centrifugation (GS-3 Rotor, 9500 rpm, 30 minutes). The collected precipitate was resuspended in 8 L water, boiled for 30 minutes and precipitated a second time as above. After centrifugation the precipitate was washed with ethanol and dried overnight at 50° C. Gel Permeation Chromatography (GPC) was used to compare the resulting product with debranched starch before precipitation verifying removal of the short amylopectin branches.

Preparation of poly(α(1→4)-D-glucose)acetate (Polymer D)

Enzymatically debranched amylose from cornstarch (5.0 g), α(1→4)-D-glucose, was suspended in 100 ml water and boiled for 1 h under nitrogen. On cooling, the suspension was cooled to 0° C. and the swollen starch granules were collected by filtration. The wet filter cake was washed 4× with glacial acetic on the filter and the acid-exchanged filter cake was pressed to remove excess acetic acid. This was added to a reaction flask equipped with a paddle stirrer and charged with acetic anhydride (99.7%, 200 ml), acetic acid (99%, 70 ml) and dichloromethane (100 ml), all prechilled to 2° C. Perchloric acid (70% aqueous, 0.5 ml) was added dropwise while maintaining an ice bath around the reaction vessel. After 2 h the reaction mixture was clear and was precipitated by pouring into rapidly stirred methanol. The white product was washed twice in methanol and dried in vacuum at 50° C. The yield was 6.5 g of poly (α(1→4)-D-glucose acetate) which was readily soluble in dichloromethane and mixtures of trifluoroacetic acid with dichloromethane or water.

A 1.0 g portion of the thus acetylated polymer was dissolved in dichloromethane (4.0 g). The viscous solution was not liquid crystalline as evidenced by the absence of birefringence when viewed through crossed polarizers. The fiber forming solution was extruded using the general procedures for Example 1 and the specific parameters in Table 1. The extrudate was not sufficiently strong to allow for several passages through the coagulation bath and best spinning continuity was observed without the use of an air gap. As-spun filament tenacity/elongation/modules values were 0.5/70.6/13.9 grams per denier/percent/grams per denier, respectively.

Comparative Example 4

1.5 g of the acetylated poly (α(1→4)-D-glucose) of Comparative Example 3 was dissolved in a mixture of trifluoroacetic acid and water (4.5 g) 100/8 w/w to provide a 25% solids solution. The resulting spin dope was not liquid crystalline as evidenced by the absence of birefringence when viewed through crossed polarizers. The solution was transferred to a 5 ml syringe fitted with a scintered metal filter and extruded through 0.25 inch air gap using the general procedures of Example 1 and the specific parameters in Table 1. As in Comparative Example 2, the spinning threadline was not sufficiently strong to allow multiple passes in the coagulation bath. The as-spun fiber exhibited a dull appearance and measured filament tenacity/elongation/modulus values were 0.3/14.7/12.6 grams per denier/percent/grams per denier, respectively.

TABLE 1

| Source | Polymer | Solvent | Polymer Concen. % Solids | Dia Holes (in.) | Hole L/d | Pump Rate Ml/min | Jet Vel Fpm | Length (ft) | Temp (° C.) | Airgap (in.) | Speed (fpm) WIND-UP | S.S.F.* |
|---|---|---|---|---|---|---|---|---|---|---|---|---|
| Ex. 1 | α(1-3) glucan acetate | TFA/H$_2$O 100/8 w/w | 35 | 0.005 | 2 | 0.08 | 20 | 14 | −1 | 0.5 | 58 | 2.9 |
| Ex. 2 | α(1-3) glucan | SAPONIFIED | | | | | | | | | | |
| Ex. 3 | α(1-3) glucan acetate | TFA/CH$_2$Cl$_2$ 60/40 v/v | 25 | 0.005 | 2 | 0.04 | 10.36 | 13 | 9 | 0.5 | 36 | 3.5 |
| Ex. 4 | α(1-3) glucan | SAPONIFIED UNDER TENSION | | | | | | | | | | |
| Ex. 5 | α(1-3) glucan acetate | TFA/CH$_2$Cl$_2$ 60/40 v/v | 25 | 0.005 | 2 | 0.04 | 10.36 | 13 | 3 | 0.5 | 23 | 2.2 |
| Ex. 6 | α(1-3) glucan acetate | TFA/CH$_2$Cl$_2$ 60/40 v/v | 20 | 0.005 | 5 | 0.08 | 20.72 | 5 | 17 | 0 | 29 | 1.4 |
| Comp. Ex. 1 | α(1-3) glucan acetate | TFA/CH$_2$Cl$_2$ 60/40 v/v | 15 | 0.005 | 4 | 0.08 | 20.72 | 5 | 18 | 0 | 15 | 0.7 |
| Comp. Ex. 2 | α(1-3) glucan | SAPONIFIED | | | | | | | | | | |
| Comp. Ex. 3 | α(1-4) glucan acetate | CH$_2$Cl$_2$ | 20 | 0.005 | 2 | 0.08 | 20 | 0.91 | 23 | 0 | 15 | 0.7 |
| Comp. Ex. 4 | α(1-4) glucan acetate | TFA/H$_2$O 100/8 w/w | 25 | 0.005 | 4 | 0.08 | 5 | 1.08 | 20 | 0.25 | 48 | 2.4 |

*Spin Stretch Factor

What is claimed is:

1. A polysaccharide fiber, comprising: a polymer comprising hexose units wherein at least 50% of the hexose units are linked via an $\alpha(1\rightarrow 3)$ glycoside linkage, said polymer having a number average degree of polymerization of at least 100, and wherein said fiber has a tensile strength of at least 1 gram per denier.

2. The polysaccharide fiber of claim 1 wherein substantially all of the hexose units are linked via an $\alpha(1\rightarrow 3)$ glycoside linkage.

3. The polysaccharide fiber of claim 1 wherein the polymer is poly($\alpha(1\rightarrow 3)$-D-glucose.

4. A process for producing a polysaccharide fiber, comprising the steps of: dissolving a sufficient amount of a polymer comprising hexose units wherein at least 50% of the hexose units are linked via an $\alpha(1\rightarrow 3)$ glycoside linkage in a solvent or in a mixture comprising a solvent to form a liquid crystalline solution having a solids content of at least 20%; and spinning a polysaccharide fiber from said liquid crystalline solution.

5. The process of claim 4 wherein substantially all of the hexose units are linked via an $\alpha(1\rightarrow 3)$ glycoside linkage.

6. The process of claim 5 wherein prior to dissolving, the polymer is derivatized.

7. The process of claim 6 wherein the polymer is acetylated.

8. The process of claim 7 wherein the derivatized polymer is a poly($\alpha(1\rightarrow 3)$-D-glucose acetate).

9. The process of claim 7 further comprising contacting the polysaccharide fiber with an excess of a saponification or hydrolysis medium to form a regenerated polysaccharide fiber.

10. The process of claim 4 wherein the solvent is selected from the group consisting of: an organic acid, an organic halide, a fluorinated alcohol, and mixtures thereof.

11. The process of claim 5 wherein the solids content ranges from 20 to about 35%.

12. A liquid crystalline solution, comprising: a solvent and an amount sufficient to form liquid crystals of a polymer comprising hexose units wherein at least 50% of the hexose units are linked via an $\alpha(1\rightarrow3)$ glycoside linkage, and wherein the amount of polymer provides a solids content of at least 20%.

13. The liquid crystalline solution of claim 12 wherein substantially all of the hexose units are linked via an $\alpha(1\rightarrow3)$ glycoside linkage.

14. The liquid crystalline solution of claim 12 wherein the polymer is poly($\alpha(1\rightarrow3)$-D-glucose acetate).

15. The liquid crystalline solution of claim 12 wherein the solvent is selected from the group consisting of: an organic acid, an organic halide, a fluorinated alcohol, and any combination thereof.

* * * * *

SEQUENCE LISTING

<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 1
gggaattcca tatgaacatt gatggtaaat attac        35

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
aacattgatg gtaaatatta c        21

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
agatctagtc ttagtttagc actctaggtg g        31

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
ttagtttagc actctaggtg g        21